United States Patent [19]

Millauer et al.

[11] Patent Number: 4,524,031
[45] Date of Patent: Jun. 18, 1985

[54] FLUOROSULFATOPERFLUOROCARBONYL COMPOUNDS

[75] Inventors: Hans Millauer, Eschborn; Günter Siegemund, Hofheim am Taunus; Werner Schwertfeger, Butzbach, all of Fed. Rep. of Germany

[73] Assignee: Hoechst Aktiengesellschaft, Frankfurt am Main, Fed. Rep. of Germany

[21] Appl. No.: 496,634

[22] Filed: May 20, 1983

Related U.S. Application Data

[62] Division of Ser. No. 300,919, Sep. 10, 1981, abandoned.

[30] Foreign Application Priority Data

Sep. 12, 1980 [DE] Fed. Rep. of Germany ....... 3034491

[51] Int. Cl.³ ........................................... C07C 141/00
[52] U.S. Cl. ........................... 260/456 F; 260/544 F; 560/145; 560/174; 568/413; 204/59 F; 204/72; 204/79
[58] Field of Search ....................... 260/458 F, 456 F

[56] References Cited

PUBLICATIONS

McBee et al., J. Am. Chem. Soc., 75, 3152 (1953).
Henne et al., J. Am. Chem. Soc. 74, 1426 (1952).
LaZerte et al., J. Am. Chem. Soc. 77, 910 (1955).
Lustig et al., Inorg. Chem., 3, 287 (1964).
Earl et al., ibid, 5, 2184 (1966).

Primary Examiner—Nicky Chan
Attorney, Agent, or Firm—Curtis, Morris & Safford

[57] ABSTRACT

A perfluorocarbonyl compound of the formula

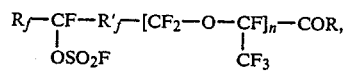

wherein
$R_f$ is perfluoroalkyl having 1 to 10 carbon atoms,
$R'_f$ is perfluoroalkylene having 1 to 10 carbon atoms,
R is fluorine, chlorine, perfluoroalkyl having 1 to 10 carbon atoms, or is alkoxy having 1 to 10 carbon atoms, and
n is 0 to 10.

3 Claims, No Drawings

FLUOROSULFATOPERFLUOROCARBONYL COMPOUNDS

This is a division of application Ser. No. 300,919 filed Sept. 10, 1981, now abandoned.

Polyfluorinated organic compounds are precursors, intermediates and end products in various specialized fields. Thus, for example, perfluorinated ketocarboxylic acid esters, such as the esters of heptafluoroisopropyl-glyoxylic acid $(CF_3)_2CFCOCOOH$ are, inter alia, valuable heat transfer fluids and surface-active agents which are distinguished by a high stability to chemicals and heat (Japanese Preliminary Published Application No. Sho-54-163521).

Fluorinated ketocarboxylic acid esters have been prepared starting from dicarbonyl compounds. Thus, Zh.Org. Khim. 13, 990 (1977) describes the reaction of perfluorodicarboxylic acid fluorides with perfluoro-olefins:

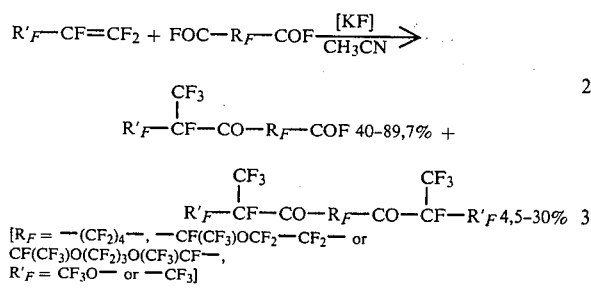

$[R_F = -(CF_2)_4-, -CF(CF_3)OCF_2-CF_2-$ or $CF(CF_3)O(CF_2)_3O(CF_3)CF-,$
$R'_F = CF_3O-$ or $-CF_3]$

However, this process has the disadvantage that, in addition to the desired ketocarboxylic acid fluoride, which can be esterified, for example, in accordance with the method in Zh.Org. Khim 11, 1626 (1975):

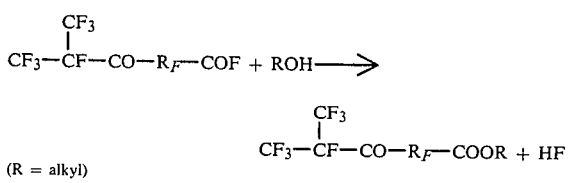

(R = alkyl)

the diketone is also obtained in a yield of up to 30%.

In an analogous manner, perfluoroketocarbonyl compounds can be prepared in accordance with the method in Zh.Org. Khim 11 1626 (1975), starting from hexafluoropropane and a perfluorodicarboxylic acid fluoride, with subsequent esterification. In this case also, the undesired diketone is obtained in yields of up to 20%.

No ketocarboxylic acid esters which contain a $CF_3-CO-$ group can be prepared by the methods mentioned above. Trifluoromethyl-ketones with an ester group have been obtainable only by two special methods.

Dokl.Akad.Nauk SSSR 196, 594 (1966) describes the preparation of 2-oxotrifluoropropanoic acid esters.

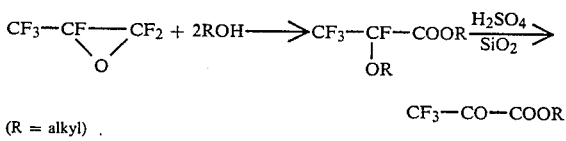

(R = alkyl)

Because the starting material is an epoxide, this reaction can give only vicinal ketocarboxylic acid esters.

The preparation of 3-oxoperfluorobutanoic acid esters is described in J.Am.Chem.Soc. 75 3152 (1953). The reaction takes place according to the equation:

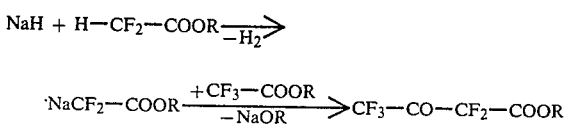

The butyl ester $(R=C_4H_9)$ is said to be isolated only in the form of the hemi-ketal (with butanol), and the ethyl ester is said to have been obtained in a yield of about 20%. From our own experiments, however, the latter compound cannot have been the ethyl ester of 3-oxo-perfluorobutyric acid (compare Example 13 which follows).

The two processes last mentioned can in each case be applied only to the preparation of 2- or 3-oxoperfluorocarboxylic acid esters.

The object of this invention is to provide a simple process for the preparation both of known and of new perfluorocarbonyl compounds, in particular of perfluoroketocarboxylic acid esters, perfluoroketocarboxylic acid halides and perfluorodiketones, the latter as far as possible containing two differently substituted keto groups.

The process is generally applicable and results in preparation of the desired compounds with a high yield and purity.

In accordance with the present invention, the above object is achieved by a process which comprises (a) electrolyzing perfluorocarbonyl compounds which also have a secondary H atom, of the formula I

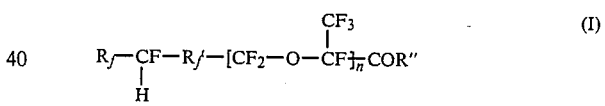

in which $R_f$ denotes perfluoroalkyl with 1-10, preferably 1-8 and in particular 1-3, C atoms, $R_f'$ denotes perfluoroalkylene with 1-10, preferably 1-6 and in particular 1-2, C atoms, R" denotes F, Cl or perfluoroalkyl with 1-10, preferably 1-8 and in particular 1-3, C atoms and n denotes a number from 0 to 10, preferably from 0 to 4 and in particular 0 or 1, in an electrolyte consisting of fluorosulfonic acid and an alkali metal fluorosulfonate, using platinum or metals of the platinum groups (Os, Ir or Pt) and/or glassy carbon as the anode materials and cathode materials which are customary but are stable under the electrolysis conditions, to give the fluorosulfato compounds of the formula II

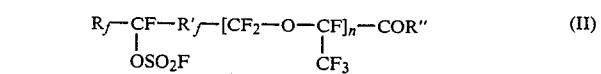

in which $R_f$, $R_f'$, R" and n have the same meaning as in formula I, (b) if necessary—if R"=F or Cl—esterifying the fluorosulfato compounds of the formula II with an organic hydroxy compound of the formula III

in which R''' denotes alkyl, aryl or aralkyl with preferably up to 10 C atoms, in particular $CH_3$ or $C_2H_5$, and (c) decomposing the compounds resulting from reaction stages a and b, of the formula IV

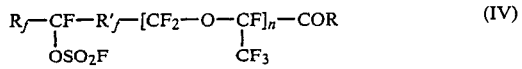

$$R_f\text{—}CF\text{—}R'_f\text{—}[CF_2\text{—}O\text{—}CF]_n\text{—}COR \qquad (IV)$$
$$\phantom{R_f\text{—}C}\underset{OSO_2F}{|}\phantom{\text{—}R'_f\text{—}[CF_2\text{—}O\text{—}}\underset{CF_3}{|}$$

in which $R_f$, $R'_f$ and n have the same meaning as in the formulae I and II and R=R'' as in the formulae I and II or —OR''', with R''' as in formula III, in the presence of catalytic amounts of alkali metal fluorides and/or aprotic N-bases to give compounds of the formula V

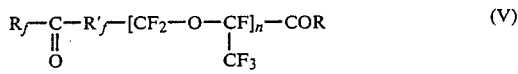

$$R_f\text{—}\underset{O}{\overset{\|}{C}}\text{—}R'_f\text{—}[CF_2\text{—}O\text{—}\underset{CF_3}{\overset{|}{CF}}]_n\text{—}COR \qquad (V)$$

in which $R_f$, $R'_f$, R and n have the same meaning as in formula IV.

The first stage (a) of the process according to the invention comprises replacement of a hydrogen atom by a fluorosulfato group. Such replacement reactions are known in polyfluorinated compounds with a primary hydrogen atom (—$CF_2H$).

In the Journal of Fluorine Chemistry 2, 173 (1972/73), C. G. Krespan describes the reaction of 1-H-perfluoropropane with peroxodisulfuryl difluoride ($FSO_2$—O—O—$SO_2F$) to give 1-fluorosulfato-perfluoropropane. ω-Fluorosulfatoperfluorocarboxylic acid nitriles are also formed from ω-H-perfluorocarboxylic acid nitriles in a corresponding manner, although in a lower yield.

After it had already been shown, by F. B. Dudley, J. Chem. Soc. 1963, 3407, that peroxodisulfuryl difluoride is formed on anodic oxidation of solutions of alkali metal fluorosulfonates in fluorosulfonic acid using platinum electrodes, A. Germain and A. Commeyras, J.Chem.Soc.Chem. Comm. 1978, 118, combined both steps to give a one-stage electrochemical process. Starting from 1-H-perfluoroalkanes, they obtained the corresponding 1-fluorosulfatoperfluoroalkanes by "anodic functionalization" in fluorosulfonic acid/potassium fluorosulfonate electrolytes on platinum by a process which proceeds indirectly via the peroxodisulfuryl difluoride intermediate.

In the process according to the invention, it is now possible, in an unexpectedly efficient manner, to apply this reaction to secondary hydrogen atoms (—CHF—) in the monohydroperfluorocarbonyl compounds I and to prepare the previously unknown fluorosulfatoperfluorocarbonyl compounds of the general formula II. It is surprising that no cathodic reduction of the carbonyl group occurs.

The electrolysis can therefore be carried out in simple, undivided cells. Although the method of the present invention can be conducted using standard laboratory beaker cells the invention is not limited thereto.

Osmium, iridium, platinum or platinum alloys containing up to about 10% of other noble metals, for example iridium, are suitable anodes. However, the anode preferably consists of glassy carbon, which has been found to be particularly corrosion-resistant under the electrolysis conditions. Glass carbon is also suitable as the cathode, although the question of materials for this electrode is not critical and other substances, such as platinum, copper or high-grade steel, are also suitable.

The ratio of the anode area to cathode area is between about 1:1 and about 10:1, preferably about 5:1 to 10:1.

The base electrolyte, which consists of fluorosulfonic acid and an alkali metal fluorosulfonate dissolved therein, is advantageously prepared by dissolving a corresponding readily accessible alkali metal chloride, such as, for example, lithium chloride, sodium chloride or potassium chloride, in fluorosulfonic acid, which, if necessary, has first been subjected to purification by fractional distillation, most of the hydrogen chloride being taken from the solution immediately. The remainder is driven out by introduction of dry nitrogen. The concentration of alkali metal sulfonate to be used in the base electrolyte is not critical and is preferably in the range from about 0.05 to about 3 moles per liter. If necessary, oxidizable impurities or traces of moisture are removed by preliminary electrolysis.

The monohydroperfluorocarbonyl compounds of the general formula I required as starting substances are dissolved or dispersed in the base electrolyte, it being possible to use mixtures containing up to about 60% by weight of monohydroperfluorocarbonyl compound, relative to the base electrolyte.

The electrolysis is in general carried out at an anodic current density of about 10–150 $mA.cm^{-2}$, preferably about 20–80 $mA.cm^{-2}$, and at a temperature of about 0° to 100° C., preferably about 20° to 40° C.

Working up of the electrolysis mixtures and isolation of the fluorosulfatoperfluorocarbonyl compounds are carried out in a manner known per se. In the case of two-phase reaction mixtures, it is advantageous for the fluoro-organic phase, which still contains only a little fluorosulfonic acid, to be separated off by decantation; otherwise, the electrolysis product must be separated off from the base electrolyte by distillation. In both cases, the electrolyte phase or the distillation bottom product can be recycled again into the electrolysis after the addition of fresh fluorosulfonic acid.

The crude fluorosulfatoperfluorocarbonyl commpounds II can be further purified by fractional distillation.

The reaction of acid halides of the general formula II in which R'' is fluorine or chlorine with an organic hydroxy compound of the formula III leads to a high yield of fluorosulfatoperfluorocarboxylic acid esters of the general formula IV in which R=OR'''. It was surprising that this reaction could be carried out without the fluorosulfato group being attacked. The esterification can be carried out in the presence or absence of an inert solvent, such as, for example, methylene chloride. The internal temperature of the batch is kept between about −80° and +70° C., preferably between about −20° and +40° C. and in particular between about 0° and 20° C., during the reaction.

The carboxylic acid halide II (in which R''=F or Cl) and the organic hydroxy compound III are advantageously employed in a molar ratio of about 1:1 to about 1:1.5. However, a larger excess of the hydroxy compound III does no harm. The sequence in which the reactants are brought together is practically of no importance for the reaction according to the invention. Nevertheless, it is advantageous to ensure uniform thorough mixing of the batch by stirring well.

If a carboxylic acid fluoride II in which R''=F is used for the esterification, hydrofluoric acid, which attacks borosilicate glass, is formed during the reaction. In this case, it is advantageous to carry out the reaction in a vessel made of material which is resistant to hydrofluoric acid.

In a preferred procedure, the carboxylic acid halide is initially introduced into an inert solvent, and a solution of the hydroxy compound III in the same solvent is added, with cooling. The hydrogen halide acid formed is removed by washing the mixture with water. The organic phase is separated off and distilled.

According to the invention, the fluorosulfatoperfluorocarbonyl compounds IV in which R=R″ or =—OR‴ are then reacted in the presence of a suitable nucleophile (alkali metal fluorides and/or aprotic N-bases) as a catalyst to give the ketocarbonyl compounds of the general formula V.

Splitting reactions of secondary fluorosulfates with alkali metal fluorides are known from the literature. The attempt to split 2-fluorosulfonyl-perfluoropropanoic acid fluoride with alkali metal fluorides is described in Inorg. Chem. 3, 287 (1964). Whilst no reaction is observed with potassium fluoride, complete destruction of the molecule occurs with cesium fluoride:

$$\text{splitting products} \xleftarrow{\text{CsF}} \underset{\underset{OSO_2F}{|}}{CF_3—CF—COF} \xrightarrow{KF} $$

In Inorg. Chem. 4, 1441 (1965), a secondary fluorosulfate is reacted with an approximately 50 molar excess of KF per mole of fluorosulfate. Conversion into the ketone is complete only after about 20 hours (no yield given):

$$\underset{\underset{OSO_2F}{|}}{CF_3—CF—CF_2—NF_2} \xrightarrow{KF} CF_3—CO—CF_2—NF_2$$

The decomposition of a secondary fluorosulfate described in Inorg. Chem. 18, 3281 (1979) is carried out with a large excess of potassium fluoride. In this case, rearrangement also additionally occurs:

The decomposition of secondary fluorosulfates is also described in Inorg. Chem. 5, 2184 (1966):

$$\underset{\underset{Br\quad OSO_2F}{|\quad\ \ |}}{CF_3—CF—CF—CF_3} \xrightarrow{\text{CsF}}{70°,\ 12\ hours}$$

$$\underset{\underset{Br\quad\ \ O}{|\quad\ \ ||}}{CF_3—CF—C—CF_3} + SO_2F_2$$

$$\underset{\underset{OSO_2F}{|}}{CF_3—CF—CO—CF_3} \xrightarrow{\text{CsF}}{70°,\ 18\ hours}$$

$$CF_3—CO—CO—CF_3 + SO_2F_2$$

While a large excess of cesium fluoride is employed in the second case, no proportions are given in the first case. However, it must be assumed that, as is customary, an amount of cesium fluoride greater than the equimolar amount is employed per mole of fluorosulfate.

According to U.S. Pat. No. 3,549,711, 0.17 mole of fluorosulfatoperfluorocyclobutane is reacted with 0.18 mole of potassium fluoride in the presence of an aprotic, polar solvent to give perfluorocyclobutanone:

No yield is stated, since the ketone is not isolated but is further reacted.

Reactions of secondary fluorosulfates with tertiary nitrogen bases are as yet unknown.

On the basis of the abovementioned examples of the splitting of secondary fluorosulfates, it was thus surprising that secondary fluorosulfatoperfluorocarbonyl compounds of the formula IV can be converted into the perfluorinated ketocarbonyl compounds V in a high yield in the presence of catalytic amounts of an alkali metal fluoride and/or of aprotic N-bases.

Catalysts which can be used are alkali metal fluorides and/or aprotic nitrogen bases, such as, for example, triethylamine, 1,4-diazabicyclo[2.2.0]octane (DABCO) or 1,8-diazabicyclo[5.4.0]undec-7-ene (DBU). The catalyst is preferably employed in an amount of about 1 to 50 mole percent, in particular from about 10 to about 30 mole percent, relative to the compound IV to be decomposed.

The reaction temperatures are between about −40° and +120° C., depending on the catalyst used.

The reaction can be carried out in an inert, aprotic solvent, but it is preferable not to use a solvent.

Furthermore, the reaction can be carried out either under normal pressure or under increased pressure.

The sequence in which the reactants are brought together is practically of no importance for reaction stage (c). Nevertheless, it is advantageous to ensure thorough mixing of the batch throughout the entire period of the reaction.

In a preferred procedure, the catalyst and the fluorosulfate IV are brought together and the mixture is heated slowly, until evolution of gas occurs. When the evolution of gas has ended, the batch is distilled over a column.

The ketocarbonyl compounds V prepared by the process according to the invention are colorless and in some cases moisture-sensitive liquids. They are therefore to be prepaed in the absence of moisture.

The starting compounds I for the process according to the invention can be obtained, for example, by the following known procedures:

(a) J.Am.Chem.Soc. 77 910 (1955) describes the preparation of CF₃—CHF—CF₂—COCl starting from the sodium salt of the corresponding carboxylic acid:

$$CF_3—CHF—CF_2—COONa \xrightarrow[\text{(heat)}]{C_6H_5—COCl} $$

$$CF_3—CHF—CF_2—COCl$$

(b) J. Org. Chem. 42 4055 (1977) describes, inter alia, the following reactions:

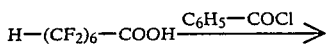

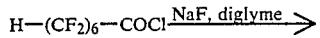

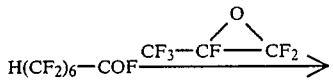

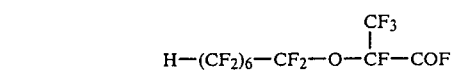

If these reactions are applied to CF₃—CHF—CF₂—COCl or

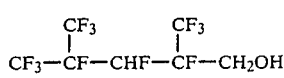

(prepared according to Nippon Nagaku Kaishi 1974, 1240), the following compounds, which are used as the starting material for the process according to the invention, are, for example, obtained:

$$CF_3-CHF-CF_2-COF$$

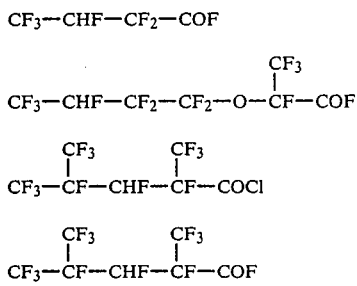

(c) J. Am. Chem. Soc. 84 4285 (1962) describes the reaction of hexafluoropropene with poly- and perfluorocarboxylic acid fluorides:

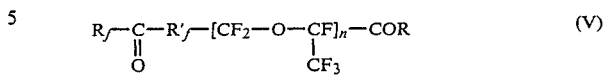

($R_F$ = perfluoroalkyl)

This reaction can also be used for the preparation of starting compounds for the process according to the invention:

$$CF_3-CHF-CF_2-COF \longrightarrow$$

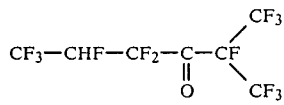

Most of the perfluorinated ketocarboxylic acid esters and diketones prepared by the process according to the invention, that is to say the compounds of the formula V in which R=OR''' or perfluoroalkyl, are new and are valuable heat transfer fluids, lubricating oils or intermediates for the preparation of other fluoroorganic compounds. The compounds of the formula V in which R=F or Cl are chiefly intermediates for the preparation of other fluoro-organic compounds.

The new compounds are:

in which $R_f$=perfluoroalkyl with 1–10, preferably 1–8 and in particular 1–3, C atoms, $R'_f$=perfluoroalkylene with 1–10, preferably 1–6 and in particular 1–2, C atoms, R=F, Cl, perfluoroalkyl with 1–10, preferably 1–8 and in particular 1–3, C atoms or —OR''' (R'''=alkyl, aryl or aralkyl with preferably up to 10 C atoms, in particular CH₃ or C₂H₅), and n=a number from 0 to 10, preferably from 0 to 4 and in particular 0 or 1, with the exception of the cases:

(a) $R_f$=(CF₃)₂CF—, $R'_f$=—(CF₂)₂₋₄—, R=F or OCH₃ and n=0.

(b) $R_f$=(CF₃)₂CF—, $R'_f$=—(CF₂)₅—, R=F and n=0, and (c) $R_f$=(CF₃)₂CF—, $R'_f$=—CF₂—, R=F and n=1.

The following examples are intended to illustrate the invention in more detail:

EXAMPLE 1

Preparation of 3-fluorosulfato-perfluorobutanoic acid fluoride (CF₃—CF(OSO₂F)—CF₂—COF)

The electrolysis device comprises a cylindrical glass vessel which has an internal diameter of about 60 mm and is 100 mm in height and is provided with an outer cooling jacket and a lid. The cell is provided with a dry ice condenser, acting as a reflux condenser, and also with a gas inlet tube, thermometer and the current leads for the electrodes. The anode comprises a plate (100×20×3 mm) of glassy carbon, which is attached to the lid of the cell and has about ⅔rds of its surface immersed in the electrolyte. A 1.5 mm thick platinum wire arranged parallel to the anode at a distance of about 20 mm serves as the cathode.

A bar magnet encased in PTFE (=polytetrafluoroethylene) on the bottom of the cell serves as the stirrer. The cell is cooled via an external cooling circulation with perchloroethylene as the cooling liquid. All the parts of the device which come into contact with the medium are made of glass, platinum or PTFE.

The base electrolyte is prepared by adding 12.5 g (0.16 mole) of potassium chloride to 250 g of distilled fluorosulfonic acid; a colorless solution is formed and is freed from residual hydrogen chloride by introduction of dry nitrogen and then pre-electrolyzed at a current strength of 2 A for 4 hours.

After addition of 190 g (0.96 mole) of 3-hydroperfluorobutanoic acid fluoride, electrolysis is carried out at a current strength of 2–3 A and at a temperature of 20° C., until a charge which has passed of 88 Ah is reached. The cell voltage is 6–16 V.

When electrolysis has ended, the fluoro-organic phase is separated off from the electrolysis mixture and, after addition of 50 g of fluorosulfonic acid, a further 141 g (0.71 mole) of 3-hydro-perfluorobutanoic acid fluoride are added to the electrolyte phase and electrolysis is carried out under the same conditions as before up to a charge amount of 71 Ah. The fluoro-organic phase is separated off again by decantation and is subjected to fractional distillation together with the 1st portion, 368 g (75% of theory) of 3-fluorosulfato-perfluorobutanoic acid fluoride of boiling point 80°-81° C. being obtained.

$^{19}$F-NMR (CDCl$_3$)(*): +51.52 (1F, —O—SO$_2$F); +25.78 (1F, —CO—F); −77.58 (3F, —CF$_3$); −116.06 (2F, —CF$_2$—); −138.47 (1F,

(*) CFCl$_3$ is used as the internal standard for all the $^{19}$F-NMR spectra.

EXAMPLE 2

Preparation of 3-fluorosulfato-perfluorobutanoic acid chloride

Using an electrolysis device as described in Example 5 which follows, and after preparation of a base electrolyte from 250 g of fluorosulfonic acid and 14.6 g (0.25 mole) of sodium chloride, 150 g (0.70 mole) of 3-H-perfluorobutanoic acid chloride are electrolyzed at a current strength of 2 A and a cell voltage of 13–16 V. After 23 hours, the electrolysis is ended and the reaction mixture is separated into its components in a separating funnel. Fractional distillation of the fluoro-organic phase gives, in addition to 62 g of starting material, 85 g (66% of theory, relative to starting material reacted) of 3-fluorosulfato-perfluorobutanoic acid chloride of boiling point 107°-108° C.

$^{19}$F-NMR (CDCl$_3$): +51.12 (1F, —O—SO$_2$—F); −77.50 (3F, —CF$_3$—); −111.55 (2F, —CF$_2$); −137.80 (1F,

EXAMPLE 3

Preparation of 6-fluorosulfato-perfluoro-2-methyl-3-oxaheptanoic acid fluoride

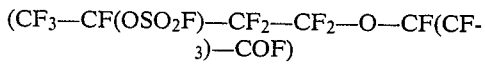

An electrolysis device as described in Example 4 is used, and a base electrolyte as described in Example 1 is prepared.

After addition of 100 g (0.27 mole) of 6-hydroperfluoro-methyl-3-oxa-heptanoic acid fluoride, electrolysis is carried out at 2 A and at a cell voltage of 11–13 V for 32 hours. The temperature is 20° C. The electrolysis mixture is then separated into its components in a separating funnel and the fluoroorganic phase (135 g) is subjected to fractional distillation. In addition to 17 g of starting material, 74 g (70% of theory, relative to the material reacted) of 6-fluorosulfato-perfluoro-2-methyl-3-oxa-heptanoic acid fluoride of boiling point 126°-128° C. are obtained.

$^{19}$F-NMR (CDCl$_3$): +51.8 (1F, —O—SO$_2$F); +27.4 (1F, —CO—F); −76.63 (0.5 F, d, J$_{gem}$=150 Hz, —O—CF$_2$—); −77.27 (3F, —CF$_3$); −77.28 (0.5F, d, J$_{gem}$=150 Hz, —O—CF$_2$—); −81.19 (3F, —CF$_3$); −84.06 (0.5F, d, J$_{gem}$=150 Hz, —O—CF$_2$—); −84.45 (0.5F, d, J$_{gem}$=150 Hz, —O—CF$_2$—); −122.72 (2F, —CF$_2$—); −124.61 (1F,

−137.46 (1F,

EXAMPLE 4

Preparation of 3-fluorosulfato-perfluoro-2,4-dimethylpentanoic acid fluoride

An electrolysis device as described in Example 1 is used, but a plate (100×20×3 mm) of glassy carbon is used as the anode and a platinum bar (diameter: 1.5 mm, length: 100 mm) is used as the cathode.

After a base electrolye has been prepared from 250 g of fluorosulfonic acid and 14.6 g (0.25 mole) of sodium chloride as described in Example 1, 230 g (0.66 mole) of 3-hydro-perfluoro-2,4-dimethyl-pentanoic acid fluoride are added and electrolysis is carried out at a current strength of 2 A and at a temperature of 25° C. until the charge which has passed is 40 Ah. The electrolysis mixture is then separated into its components in a separating funnel and the fluoro-organic phase (269 g) is subjected to fractional distillation. In addition to 53 g of starting material, 110 g (48% of theory, relative to the material reacted) of 3-fluorosulfato-perfluoro-2,4-dimethyl-pentanoic acid fluoride of boiling point 130° C. are thereby obtained.

$^{19}$F-NMR (CDCl$_3$): 30 54.04 (1F, —O—SO$_2$F); +34.6, +32.31 (1F, —CO—F); −70.73 (9F, broad, —CF$_3$); −121.93, −123.57 (1F, —CF—O—); −173.48, −176.05, −177.69 (2F,

EXAMPLE 5

Preparation of 5-fluorosulfato-perfluoro-2-methyl-hexan-3-one

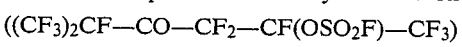

An electrolysis device as described in Example 1 is used, but a bar (diameter: 3 mm, length: 100 mm) of glassy carbon is used as the cathode.

After a base electrolye has been prepared from 250 g of fluorosulfonic acid and 10.6 g (0.25 mole) of lithium chloride as described in Example 1, 107 g (0.31 mole) of 5-H-perfluoro-2-methyl-hexan-3-one are electrolyzed at a current strength of 2 A and a cell voltage of 12–14 Volts. After 27 hours, the electrolysis is ended and the electrolysis mixture is separated into its components in a separating funnel. Fractional distillation of the fluoro-organic phase gives 101 g (73% of theory) of 5- fluorosulfato-perfluoro-2-methyl-hexan-3-one of boiling point 109°–110° C.

19F-NMR (CDCl3): +51.9 (1F, —O—SO2F); −73.1 (6F, —CF3); −75.9 (3F, —CF3); −114.8 (2F, —CF2—); −136.6 (1F, —CF(CF3)2); −189.4 (1F, CF—O—SO2—F).

EXAMPLE 6

Preparation of 3-fluoro-sulfatoperfluorobutanoic acid methyl ester

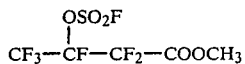

A solution of 25.6 g (0.8 mole) of methanol in 30 ml of methylene chloride is added dropwise to a solution of 177.6 g (0.6 mole) of 3-fluorosulfatoperfluorobutanoic acid fluoride in 100 ml of ethylene chloride. Throughout the entire reaction, the internal temperature is kept below +10° C. by cooling. The batch is subsequently stirred at room temperature for one hour and is then extracted several times by shaking with water. After the organic phase has been dried over sodium sulfate, it is distilled over a packed column. 155 g (84%) of 3-fluorosulfatoperfluorobutanoic acid methyl ester are obtained with a boiling point of 70° C. (60 mm Hg).

Analysis: calculated: C 19.49, H 0.98, F 43.16, S 10.41. found: C 19.7, H 0.9, F 42.9, S 10.3.

1H-NMR (CDCl3): 3.98 (S).
19F-NMR (CDCl3): +51.1 (—OSO2F), −77.7 (CF3), −116.4 (CF2), −138.7 (CF).
(IR (neat): 5.59μ (CO), 6.73μ (SO).

EXAMPLE 7

Preparation of 3-fluorosulfatoperfluorobutanoic acid methyl ester

The reaction is carried out as described in Example 6. The following amounts are employed: 258 g (0.83 mole) of 3-fluorosulfatoperfluorobutanoic acid chloride, dissolved in 100 ml of methylene chloride; 38.4 g (1.2 moles) of methanol, dissolved in 30 ml of methylene chloride.

Distillation gives 216 g (85%) of 3-fluorosulfatoperfluorobutanoic acid methyl ester.

EXAMPLE 8

Preparation of 3-fluorosulfatoperfluorobutanoic acid ethyl ester

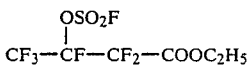

63 g (0.2 mole) of 3-fluorosulfatoperfluorobutanoic acid chloride and 50 ml of methylene chloride are initially introduced into a flask. A solution of 13.8 g (0.3 mole) of ethanol in 20 ml of methylene chloride is then added dropwise. During this addition, the internal temperature is kept between 5° and 10° C. The batch is subsequently stirred at room temperature for one hour and is then washed several times with water and dried over sodium sulfate. Distillation gives 48 g (74%) of 3-fluorosulfatoperfluorobutanoic acid ethyl ester with a boiling point of 152° C. (761 mm).

Analysis: Calculated: C 22.37, H 1.56, F 41.28, S 9.95. Found: C 22.1, H 1.5, F 41.0, S 9.9.

1H-NMR (CDCl3): 1.49 (t, J=7 Hz, 3H, CH3), 4.43 (q, J=7 Hz, 2H, CH2)
19F-NMR (CDCl3): +50.34 (—OSO2F); −78.46 (CF3); −117.35 (CF2); −139.35 (CF).
IR (neat): 5.60μ (CO), 6.75μ (SO).

EXAMPLE 9

6-Fluorosulfatoperfluoro-2-methyl-3-oxa-heptanoic acid methyl ester

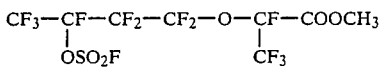

99 g (0.21 mole) of 6-fluorosulfatoperfluoro-2-methyl-3-oxa-heptanoic acid fluoride are dissolved in 80 ml of methylene chloride. The mixture is cooled to +5° C. and a solution of 9.6 g (0.3 mole) of methanol in 30 ml of methylene chloride is added dropwise. During the reaction, the internal temperature is kept between 5° and 10° C. The batch is subsequently stirred at room temperature for one hour and is then washed several times with water and dried over sodium sulfate. Distillation over a packed column gives 83 g (84%) of the methyl ester with a boiling point of 81°–88° C. (30 mm Hg) as a diastereomer mixture (ratio: about 1:1).

Analysis: Calculated: C 20.26, H 0.64, F 52.09, S 6.76. Found: C 20.1, H 0.3, F 51.8, S 7.3.

1H-NMR (CDCl3): 3.96 (S).
19F-NMR (CDCl3): +51.7 (1F, —O—SO2F), −76.8 (0.5F, —CF2—O—, Jgem=150 Hz), −77.2 (3F, CF3); −77.7 (0.5F, —CF2—O—, Jgem=150 Hz), −81.6 (3F, —O—CF(CF3)COO); −83.8 (0.5F, —CF2—O—, Jgem=150 Hz); −84.5 (0.5F, —CF2—O—, Jgem=150 Hz); −121.4 (CF2); −131 (—CF—COO—); −137.5

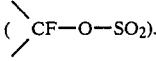

IR (neat): 5.67μ (C=O), 6.71μ (S=O).

EXAMPLE 10

3-Fluorosulfatoperfluoro-2,4-dimethylpentanoic acid methyl ester

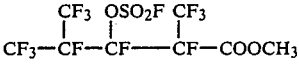

A solution of 3.8 g (0.12 mole) of methanol in 30 ml of methylene chloride is added dropwise to a mixture of 30.5 g (0.683 mole) of 3-fluorosulfatoperfluoro-2,4-dimethylpentanoic acid fluoride and 30 ml of methylene chloride at an internal temperature of 5°–10° C. The batch is subsequently stirred at room temperature for 30 minutes and is then washed several times with water. After it has been dried over sodium sulfate, it is distilled over a packed column. 24.7 g (78.7%) of 3-fluorosulfatoperfluoro-2,4-dimethylpentanoic acid methyl ester are obtained with a boiling point of 75°–76° C. (20 mm).

Analysis: Calculated: C 20.97, H 0.66, F 53.91, S 7.00. Found: C 20.9, H 0.7, F 53.9, S 7.4.

1H-NMR (CDCl3): 4.03 (S).
19F-NMR (CDCl3): +52.45 (1F, —OSO2F); −70.3 to −72.3 (9F, 3x CF3); −121.1 and 123.5 (1F, —C-

F—O—); −174.4; −176.0; −117.9 and −178.8 (2F, CF).

IR (neat): 5.53μ and 5.60μ (CO), 6.71μ (SO).

EXAMPLE 11

3-Oxo-perfluorobutanoic acid methyl ester (CF₃—CO—CF₂—COOCH₃)

The reaction is carried out in a fume cupboard.

154 g (0.5 mole) of 3-fluorosulfatoperfluorobutanoic acid methyl ester and 2.9 g (0.05 mole) of potassium fluoride are introduced into a dry flask with a magnetic stirrer, thermometer, reflux condenser and subsequent bubble counter. The batch is heated slowly. Splitting off of sulfuryl fluoride starts at an internal temperature of about 60° C. When the evolution of gas has ended, the batch is distilled over a packed column. 95.5 g (93%) of 3-oxoperfluorobutanoic acid methyl ester are obtained with a boiling point of 93° C. (755 mm Hg).

Analysis: Calculated: C 29.14, H 1.47, F 46.10. Found: C 28.80, H 1.45, F 46.15.

¹H-NMR (CDCl₃): 3.95 (S).

¹⁹F-NMR (CDCl₃): −74.2 (CF₃); −112.6 (CF₂).

IR (gas spectrum): 5.35μ (C=O); 5.55μ (—COO—).

EXAMPLE 12

3-Oxoperfluorobutanoic acid methyl ester

The reaction is carried out in a fume cupboard.

2.25 g (0.015 mole) of 1,4-diazabicyclo[2,2,2]octane are initially introduced into a dry flask with a magnetic stirrer, thermometer, reflux condenser and subsequent bubble counter. 31 g (0.1 mole) of 3-fluorosulfatoperfluorobutanoic acid methyl ester are then added dropwise at room temperature. Evolution of gas starts immediately. When the dropwise addition has ended, the reaction is brought to completion by warming the mixture slightly. Subsequent distillation gives 16 g (78%) of 3-oxoperfluorobutanoic acid methyl ester.

EXAMPLE 13

3-Oxoperfluorobutanoic acid ethyl ester (CF₃—CO—CF₂—COOC₂H₅)

The reaction is carried out in a fume cupboard.

45 g (0.139 mole) of 3-fluorosulfatoperfluorobutanoic acid ethyl ester and 2.9 g (0.05 mole) of potassium fluoride are introduced into a dry flask with a magnetic stirrer, thermometer, reflux condenser and bubble counter. The batch is heated until evolution of gas starts. When the evolution of gas has ended, the mixture is subsequently stirred at 105° C. for one hour. Distillation over a packed column gives 27 g (88%) of 3-oxoperfluorobutanoic acid ethyl ester with a boiling point of 106° C. (754 mm).

Analysis: Calculated: C 32.74, H 2.29, F 43.16. Found: C 32.6, H 2.2, F 43.1.

¹H-NMR (CDCl₃): 1.38 (t, J=7 Hz, 3H, CH₃); 4.43 (q, J=7 Hz, 2H, CH₂);

¹⁹F-NMR (CDCl₃): −75.05 (3F, CF₃); −113.73 (2F, CF₂);

IR (neat): 5.33μ (CO); 5.56μ (—COO—).

From these unambiguous data, the compound CF₃COCF₂COOC₂H₅ allocated a boiling point of 130°-131° C. in J. Am. Chem. Soc. 75, 3152 (1955) cannot have been this compound.

EXAMPLE 14

Perfluoro-2-methyl-3-oxa-heptan-6-one-carboxylic acid methyl ester

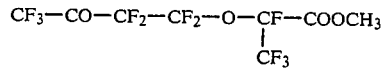

The reaction is carried out in a fume cupboard.

70 g (0.15 mole) of 6-fluorosulfatoperfluoro-2-methyl-3-oxaheptanoic acid methyl ester are initially introduced, at −5° C., into a dry flask with a magnetic stirrer, thermometer, reflux condenser and bubble counter. 2.2 g (0.02 mole) of 1,4-diazabicyclo[2,2,2]octane are then added. Slight evolution of gas starts immediately. The reaction is allowed to go to conclusion at about 0° C. The batch is subsequently stirred at room temperature for one hour and is then distilled. 45 g (82%) of the keto-ester are obtained with a boiling point of 131°-132° C. (745 mm Hg).

Analysis: Calculated: C 25.82, H 0.81, F 56.16. Found: C 25.35, H 0.80, F 55.90.

¹H-NMR (CDCl₃): 3.95 (S)

¹⁹F-NMR (CDCl₃): −75.56 (3F, —CO—CF₃); −79.5 (dm, J=145 Hz, 1F, —O—CF₂—); −84.83 (3F, CF₃); −88.4 (dm, J=145 Hz, 1F, —O—CF₂); −120.13 (dm, J=288 Hz, 1F, —CO—CF₂—); −123.7 (dm, J=288 Hz, 1F, —CO—CF₂—); −132.5 (1F, CF).

IR (neat): 5.56μ (C=O).

EXAMPLE 15

Perfluoro-3-oxo-2,4-dimethylpentanoic acid methyl ester

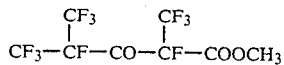

The reaction is carried out in a fume cupboard.

0.6 g (0.01 mole) of potassium fluoride and 22 g (0.048 mole) of 3-fluorosulfatoperfluoro-2,4-dimethylpentanoic acid methyl ester are introduced into a dry flask with a magnetic stirrer, thermometer, Vigreux column, column head and bubble counter. When the batch is heated, evolution of gas is observed from an internal temperature of 100° C., becoming vigorous from 110° C. When the evolution of gas has subsided, the batch is distilled. 14.4 g (84%) of perfluoro-3-oxo-2,4-dimethylpentanoic acid methyl ester are obtained with a boiling point of 128° C. (748 mm).

Analysis: Calculated: C 26.98, H 0.85, F 58.69. Found: C 26.9, H 0.9, F 58.8.

¹H-NMR (CDCl₃): 3.98 (S).

¹⁹F-NMR (CDCL₃): −73.27 (3F, CF₃); −73.61 (3F, CF₃); −75.19 (3F, CF₃); −175.93 (1F, —CO—CF—CO—); −187.62 (1F, CF).

IR (neat): 5.51μ (CO); 5.60μ (CO).

EXAMPLE 16

Perfluoro-3-oxo-2,4-dimethylpentanoic acid fluoride

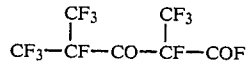

The reaction is carried out in a fume cupboard.

0.6 g (0.01 mole) of dry, finely powdered potassium fluoride is initially introduced, at room temperature, into a dry flask with a magnetic stirrer, thermometer, dropping funnel, reflux condenser and bubble counter. After dropwise addition of 30 g (0.067 mole) of 3-fluorosulfatoperfluoro-2,4-dimethylpentanoic acid fluoride, the batch is heated. Evolution of gas starts from an internal temperature of about 100° C. When the evolution of gas has ended, the batch is distilled over a packed column. 14.2 g (61%) of perfluoro-3-oxo-2,4-dimethylpentanoic acid fluoride are obtained with a boiling point of 72°–74° C. (760 mm).

$^{19}$F-NMR (CDCl$_3$): +32.09 (1F, COF); −73.28 (3F, CF$_3$); −73.84 (3F, CF$_3$); −74.51 (3F, CF$_3$); −175.25 (1F, CF); −187.49 (1F, isopropyl-CF).

IR (gas spectrum): 5.24μ and 5.32μ (COF); 5.58μ (CO).

EXAMPLE 17

Perfluoro-(2-methyl-hexane-3,5-dione)

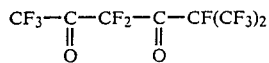

4 g of CsF are initially introduced into a 200 ml three-necked flask with a dropping funnel, thermometer, magnetic stirrer and Raschig ring column with a distillation head for low-temperature distillation, and are heated thoroughly in vacuo. 68.7 g (0.154 mole) of perfluoro-(5-fluorosulfato-2-methylhexan-3-one), (CF$_3$)$_2$CF—CO—CF$_2$—CF(CF$_3$)OSO$_2$F, are added dropwise at room temperature in the course of 1 hour. During this addition, the reaction mixture warms slowly to 40° C. In addition to 15 g of SO$_2$F$_2$ (=95% of theory), 36 g (0.105 mole) of perfluoro-(2-methyl-hexane-3,5-dione) of boiling point 76° C. (745 mm) can be isolated by fractional distillation. Yield: 68% of theory.

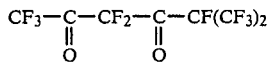

C$_7$F$_{12}$O$_2$ MW: 344 calculated: C 24.4, F 66.3. found: C 23.7, F 65.9.

$^{19}$F-NMR (C$_6$D$_6$): −74.0 (6F, CF$_3$); −75.2 (3F, CF$_3$); −113.2 (2F, CF$_2$); −191.2 (1F, CF);

IR (neat): 5.55μ (C=O).

We claim:

1. A perfluorocarbonyl compound of the formula

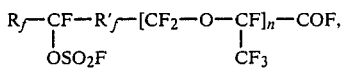

wherein

R$_f$ is perfluoroalkyl having 1 to 10 carbon atoms,
R$_f'$ is perfluoroalkylene having 1 to 10 carbon atoms, and
n is 0 to 10.

2. A compound as in claim 1 wherein
R$_f$ is perfluoroalkyl having 1 to 8 carbon atoms,
R$_f'$ is perfluoroalkylene having 1 to 6 carbon atoms, and
n is 0 to 4.

3. A compound as in claim 1 wherein
R$_f$ is perfluoroalkyl having 1 to 3 carbon atoms,
R$_f'$ is perfluoroalkylene having 1 or 2 carbon atoms, and
n is 0 or 1.

* * * * *